(12) United States Patent
Kudis et al.

(10) Patent No.: US 6,627,581 B1
(45) Date of Patent: Sep. 30, 2003

(54) CYCLOPROPYL-ANELLATED 3-(4,5-DIHYDROISOXAZOL-3-YL)-SUBSTITUTED BENZOYLPYRAZOLES

(75) Inventors: Steffen Kudis, Mannheim (DE); Ernst Baumann, Dudenhofen (DE); Wolfgang von Deyn, Neustadt (DE); Klaus Langemann, Worms (DE); Guido Mayer, Neustadt (DE); Ulf Misslitz, Neustadt (DE); Ulf Neidlein, Mannheim (DE); Matthias Witschel, Bad Dürkheim (DE); Karl-Otto Westphalen, Speyer (DE); Helmut Walter, Obrigheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/130,849

(22) PCT Filed: Nov. 27, 2000

(86) PCT No.: PCT/EP00/11823
§ 371 (c)(1),
(2), (4) Date: May 23, 2002

(87) PCT Pub. No.: WO01/40221
PCT Pub. Date: Jun. 7, 2001

(30) Foreign Application Priority Data

Dec. 2, 1999 (DE) .......................... 199 58 031

(51) Int. Cl.⁷ .................... A01N 43/80; A01N 43/56
(52) U.S. Cl. .................... 504/271; 504/280; 504/282
(58) Field of Search ................. 504/271, 280, 504/282

(56) References Cited

U.S. PATENT DOCUMENTS

| | | | |
|---|---|---|---|
| 5,846,907 A | 12/1998 | von Deyn | 504/221 |
| 6,147,031 A | 11/2000 | Adachi | |
| 6,165,944 A | 12/2000 | von Deyn | 504/271 |
| 6,255,251 B1 * | 7/2001 | De Mesmaeker et al. | 504/271 |
| 6,297,198 B1 * | 10/2001 | Lee | 504/271 |
| 6,323,155 B1 * | 11/2001 | Musil et al. | 504/271 |

FOREIGN PATENT DOCUMENTS

| | | |
|---|---|---|
| CA | 2310087 | 6/1987 |
| CA | 2278331 | 7/1998 |
| CA | 2334467 | 12/1999 |
| DE | 199 36520 | 2/2001 |
| WO | 98/31681 | 7/1998 |
| WO | 98/31682 | 7/1998 |
| WO | 99/23094 | 5/1999 |
| WO | 99/21852 | 6/1999 |
| WO | 99/26930 | 6/1999 |
| WO | 99/63823 | 12/1999 |
| WO | 00/34272 | 6/2000 |
| WO | 00/34273 | 6/2000 |
| WO | 01/10864 | 2/2001 |

OTHER PUBLICATIONS

Baird, Mark(DN 136:294327, CAPLUS, abstract of Tetrahederon (2001), 57(49), 9849–9858).*
Bolesov, I.G. et al. (Dn 113:115142, HCAPLUS, abstract of Zhurnal Organicheskoi Khimi (1990), 26(1), 102–19).*
Derwent Abst. 99–312930/26.
Derwent Image 2001–2732339 [28].
2000–442136/38—Abstract WO 200034272–A2.
2000–442137/38—WO 200034273–A2.

* cited by examiner

*Primary Examiner*—Sabiha Qazi
(74) *Attorney, Agent, or Firm*—Keil & Weinkauf

(57) ABSTRACT

Cyclopropyl-fused 3-(4,5-dihydroisoxazol-3-yl)-substituted benzoylpyrazoles of the formula I

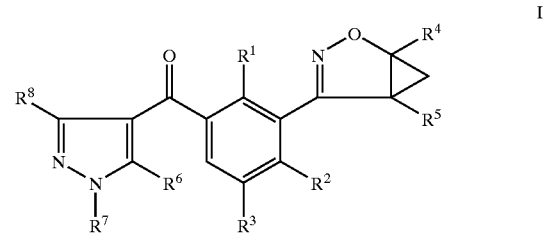

in which the variables are as defined in the description, and their agriculturally useful salts are described. The compounds have herbicidal action.

10 Claims, No Drawings

CYCLOPROPYL-ANELLATED 3-(4,5-DIHYDROISOXAZOL-3-YL)-SUBSTITUTED BENZOYLPYRAZOLES

The present invention relates to certain cyclopropyl-fused 3-(4,5-dihydroisoxazol-3-yl)-substituted benzoylpyrazoles and to intermediates and processes for their preparation, to compositions comprising them and to the use of these derivatives or compositions comprising them for controlling harmful plants.

The literature, for example WO 96/26206, WO 98/31682 and WO 98/31681, discloses pyrazol-4-yl-benzoyl derivatives.

The earlier applications WO 00/34273, WO 00/34272, DE 19936520.2 and DE 19936518.0 describe, inter alia, (4,5-dihydroisoxazol-3-yl)-substituted benzoylpyrazoles and their herbicidal properties. Derivatives having fused cycloalkane rings have not been described.

However, the herbicidal properties of the prior-art compounds and their compatibility with crop plants are not entirely satisfactory.

It is an object of the present invention to provide novel, in particular herbicidally active, compounds having improved properties.

We have found that this object is achieved by the cyclopropyl-fused 3-(4,5-dihydroisoxazol-3-yl)-substituted benzoylpyrazoles of the formula I

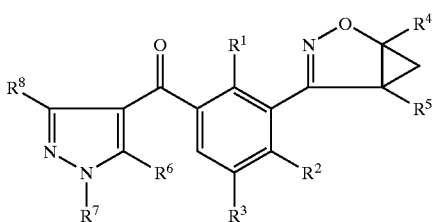

in which
$R^1$ is $C_1-C_6$-alkyl, $C_1-C_6$-haloalkyl, $C_1-C_6$-alkoxy, $C_1-C_6$-haloalkoxy, halogen or nitro;
$R^2$ is $C_1-C_6$-alkyl, $C_1-C_6$-haloalkyl, $C_1-C_6$-alkoxy, $C_1-C_6$-haloalkoxy, $C_1-C_6$-alkylthio, $C_1-C_6$-haloalkylthio, $C_1-C_6$-alkylsulfinyl, $C_1-C_6$-haloalkylsulfinyl, $C_1-C_6$-alkylsulfonyl, $C_1-C_6$-haloalkylsulfonyl, halogen, cyano or nitro;
$R^3$ is hydrogen, $C_1-C_6$-alkyl or halogen;
$R^4$ is hydrogen, $C_1-C_4$-alkyl or $C_1-C_4$-haloalkyl;
$R^5$ may have the meanings given for $R^4$; or
$R^4$, $R^5$ together are a $C_1-C_4$-alkanediyl group which may be partially or fully halogenated and/or may carry one to three $C_1-C_4$-alkyl groups;
$R^6$ is hydroxyl, $C_1-C_6$-alkoxy, $C_3-C_6$-alkenyloxy, $C_1-C_6$-alkylsulfonyloxy, $C_1-C_6$-alkylcarbonyloxy, phenyl-$C_1-C_4$-alkoxy, phenylcarbonyl-$C_1-C_4$-alkoxy, phenylsulfonyloxy, phenylcarbonyloxy, where the phenyl radical of the four lastmentioned substituents may be partially or fully halogenated and/or may carry one to three of the following groups: nitro, cyano, $C_1-C_4$-alkyl, $C_1-C_4$-haloalkyl, $C_1-C_4$-alkoxy or $C_1-C_4$-haloalkoxy;
$R^7$ is hydrogen, $C_1-C_6$-alkyl or cyclopropyl;
$R^8$ is hydrogen, $C_1-C_6$-alkyl or $C_1-C_6$-haloalkyl; and their agriculturally useful salts.

Furthermore, we have found herbicidal compositions which comprise the compounds I and have very good herbicidal activity. Moreover, we have found processes for preparing these compositions and methods for controlling undesirable vegetation using the compounds I.

Depending on the substitution pattern, the compounds of the formula I may contain one or more centers of chirality, in which case they are present as enantiomer or diastereomer mixtures. The invention provides both the pure enantiomers or diastereomers and their mixtures.

The compounds of the formula I can also be present in the form of their agriculturally useful salts, the nature of the salt generally being immaterial. In general, the salts of those cations and the acid addition salts of those acids are suitable whose cations and anions, respectively, do not adversely affect the herbicidal action of the compounds I.

Suitable cations are, in particular, ions of the alkali metals, preferably lithium, sodium and potassium, the alkaline earth metals, preferably calcium and magnesium, the transition metals, preferably manganese, copper, zinc and iron, and also ammonium where, if desired, one to four hydrogens may be replaced by $C_1-C_4$-alkyl, hydroxy-$C_1-C_4$-alkyl, $C_1-C_4$-alkoxy-$C_1-C_4$-alkyl, hydroxy-$C_1-C_4$-alkoxy-$C_1-C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium, furthermore phosphonium ions, sulfonium ions, preferably tri($C_1-C_4$-alkyl)sulfonium, and sulfoxonium ions, preferably tri($C_1-C_4$-alkyl) sulfoxonium.

Anions of useful acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1-C_4$-alkanoic acids, preferably formate, acetate, propionate and butyrate.

The organic moieties mentioned for the substituents $R^1-R8$ or as radicals on phenyl rings are collective terms for individual enumerations of the individual group members. All hydrocarbon chains, i.e. all alkyl, alkylcarbonyl, haloalkyl, alkoxy, haloalkoxy, alkylcarbonyloxy, alkylsulfonyloxy, alkylthio, haloalkylthio, alkylsulfinyl, haloalkylsulfinyl, alkylsulfonyl, haloalkylsulfonyl, alkenyl, alkenyloxy, phenylalkyl, phenylcarbonylalkyl, phenylalkoxy and phenylcarbonylalkoxy moieties can be straight-chain or branched. Unless indicated otherwise, halogenated substituents preferably carry one to five identical or different halogen atoms. The term halogen denotes in each case fluorine, chlorine, bromine or iodine.

Examples of other meanings are:
$C_1-C_4$-alkyl, and the alkyl moieties of $C_1-C_4$-alkylcarbonyl, $C_1-C_4$-alkylcarbonyloxy, phenyl-$C_1-C_4$-alkyl and phenylcarbonyl-$C_1-C_4$-alkyl: for example methyl, ethyl, propyl, 1-methylethyl, butyl, 1-methylpropyl, 2-methylpropyl and 1,1-dimethylethyl;

$C_1-C_6$-alkyl, and the alkyl moieties of $C_1-C_6$-alkylcarbonyl and $C_1-C_6$-alkylcarbonyloxy: $C_1-C_4$-alkyl as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, bromomethyl, iodomethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_6$-haloalkyl: $C_1$–$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_2$-alkoxy as alkoxy moieties of phenyl-$C_1$–$C_2$-alkoxy and phenylcarbonyl-$C_1$–$C_2$-alkoxy: methoxy and ethoxy;

$C_1$–$C_4$-alkoxy, and the alkoxy radicals of phenyl-$C_1$–$C_4$-alkoxy and phenylcarbonyl-$C_1$–$C_4$-alkoxy: $C_1$–$C_2$-alkoxy as mentioned above, and also, for example, propoxy, 1-methylethoxy, butoxy, 1-methylpropoxy, 2-methylpropoxy and 1,1-dimethylethoxy;

$C_1$–$C_6$-alkoxy: $C_1$–$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_6$-haloalkoxy: $C_1$–$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1$–$C_4$-alkylthio: for example methylthio, ethylthio, propylthio, 1-methylethylthio, butylthio, 1-methylpropylthio, 2-methylpropylthio and 1,1-dimethylethylthio;

$C_1$–$C_6$-alkylthio: $C_1$–$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_4$-haloalkylthio: a $C_1$–$C_4$-alkylthio radical as mentioned above which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio and nonafluorobutylthio;

$C_1$–$C_6$-haloalkylthio: $C_1$–$C_4$-haloalkylthio as mentioned above, and also, for example, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio or dodecafluorohexylthio;

$C_1$–$C_6$-alkylsulfinyl ($C_1$–$C_6$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 11,12-trimethylpropylsulfinyl, 1,2,2-trimethylpropylsulfinyl, 1-ethyl-1-methylpropylsulfinyl or 1-ethyl-2-methylpropylsulfinyl;

$C_1$–$C_6$-haloalkylsulfinyl: $C_1$–$C_6$-alkylsulfinyl as mentioned above which is partially or fully substituted by fluorine, chlorine, bromine and/or iodine, i.e., for example, fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl;

$C_1$–$C_4$-alkylsulfonyl ($C_1$–$C_4$-alkyl-S(=O)$_2$—), and the alkylsulfonyl moieties of $C_1$–$C_4$-alkylsulfonyloxy: for example methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl;

$C_1$–$C_6$-alkylsulfonyl, and the alkylsulfonyl moieties of $C_1$–$C_6$-alkylsulfonyloxy: a $C_1$–$C_4$-alkylsulfonyl radical as mentioned above, and also, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$–$C_6$-haloalkylsulfonyl: a $C_1$–$C_6$-alkylsulfonyl radical as mentioned above which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl or dodecafluorohexylsulfonyl;

$C_3$–$C_6$-alkenyloxy: for example prop-1-en-1-yloxy, prop-2-en-1-yloxy, 1-methylethenyloxy, buten-1-yloxy, buten-2-yloxy, buten-3-yloxy, 1-methyl-prop-1-en-1-yloxy, 2-methylprop-1-en-1-yloxy, 1-methylprop-2-en-1-yloxy, 2-methylprop-2-en-1-yloxy, penten-1-yloxy, penten-2-yloxy, penten-3-yloxy, penten-4-yloxy, 1-methylbut-1-en-1-yloxy, 2-methylbut-1-en-1-yloxy, 3-methylbut-1-en-1-yloxy, 1-methyl-but-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, hex-4-en-1-yloxy, hex-2-en-1-yloxy, hex-3-en-1-yloxy, hex-4-en-m-yloxy, hex-5-en-1-yloxy, 1-methylpent-1-en-1-yloxy, 2-methylpent-1-en-1-yloxy, 3-methylpent-2-en-1-yloxy, 4-methylpent-2-en-1-yloxy, 3-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,2-dimethylbut-2-en-1-yloxy, 1,2-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-3-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-3-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-3-en-1-yloxy, 1-ethylbut-2-en-1-yloxy, 2-ethylbut-3-en-1-yloxy, 2-ethylbut-3-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy and 1-ethyl-2-methyl-prop-2-en-1-yloxy;

$C_3$–$C_6$-alkenyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex- 1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

$C_1$–$C_4$-alkanediyl: for example methanediyl, 1,2-ethanediyl, 1,3-propanediyl and 1,4-butanediyl.

The phenyl rings of the radicals phenylalkyl, phenylcarbonylalkyl, phenylalkoxy, phenylcarbonylalkoxy, phenylsulfonyl, phenylsulfonyloxy, phenylcarbonyl and phenylcarbonyloxy are preferably unsubstituted or carry one, two or three halogen atoms and/or one nitro group, one cyano group, one or two methyl, trifluoromethyl, methoxy or trifluoromethoxy groups.

In the formula I, $R^1$ is preferably $C_1$–$C_6$-alkyl, $C_1$–$C_6$-haloalkyl, $C_1$–$C_6$-alkoxy or halogen;
in particular $C_1$–$C_4$-alkyl, preferably methyl, ethyl, n-propyl or isopropyl; or halogen, preferably fluorine, chlorine or bromine;
particularly preferably methyl or chlorine;
most preferably methyl;

$R^2$ is preferably $C_1$–$C_6$-haloalkyl, $C_1$–$C_6$-alkylsulfonyl, halogen or nitro;
in particular $C_1$–$C_4$-haloalkyl, preferably difluoromethyl or trifluoromethyl; $C_1$–$C_4$-alkylsulfonyl, preferably methylsulfonyl or ethylsulfonyl; or halogen, preferably fluorine or chlorine;
particularly preferably $C_1$–$C_4$-alkylsulfonyl, most preferably methylsulfonyl;

$R^3$ is preferably hydrogen, $C_1$–$C_4$-alkyl or halogen;
in particular hydrogen, chlorine or methyl;
particularly preferably hydrogen;

$R^4$ is preferably hydrogen, $C_1$–$C_4$-alkyl or $C_1$–$C_4$-haloalkyl;
in particular hydrogen, methyl, ethyl, chloromethyl or bromomethyl;

$R^5$ is preferably hydrogen or $C_1$–$C_4$-alkyl;
in particular hydrogen; or $R^4$,$R^5$ together are preferably a $C_1$–$C_4$-alkanediyl group;
in particular a methanediyl group;
particularly preferably are hydrogen; or $R^6$ is preferably hydroxyl, $C_1$–$C_6$-alkoxy, $C_1$–$C_6$-alkylsulfonyloxy, $C_1$–$C_6$-alkylcarbonyloxy, phenyl-$C_1$–$C_2$-alkoxy, phenylcarbonyl-$C_1$–$C_2$-alkoxy, phenylsulfonyloxy, phenylcarbonyloxy, where the phenyl radical of the four lastmentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy;

in particular hydroxyl, phenyl-$C_1$–$C_2$-alkoxy, phenylcarbonyl-$C_1$–$C_2$-alkoxy, phenylsulfonyloxy, phenylcarbonyloxy, where the phenyl radical of the four lastmentioned substituents may be partially or fully halogenated or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy;
particularly preferably hydroxyl;

$R^7$ is preferably hydrogen, $C_1$–$C_4$-alkyl or cyclopropyl; in particular $C_1$–$C_4$-alkyl, preferably methyl, ethyl, isopropyl, isobutyl, s-butyl or t-butyl; or cyclopropyl;

$R^8$ is preferably hydrogen or $C_1$–$C_4$-alkyl;
in particular hydrogen, methyl or ethyl;
particularly preferably hydrogen or methyl.

Particular preference is given to cyclopropyl-fused 3-(4,5-dihydroisoxazol-3-yl)-substituted benzoylpyrazoles of the formula I in which $R^1$ is $C_1$–$C_6$-alkyl or halogen;
$R^2$ is $C_1$–$C_6$-haloalkyl, $C_1$–$C_6$-alkylsulfonyl or halogen;
$R^3$ is hydrogen, $C_1$–$C_4$-alkyl or halogen;
$R^7$ is $C_1$–$C_4$-alkyl or cyclopropyl;
$R^8$ is hydrogen or $C_1$–$C_4$-alkyl.

Particular preference is furthermore given to cyclopropyl-fused 3-(4,5-dihydroisoxazol-3-yl)-substituted benzoylpyrazoles of the formula I in which $R^1$ is methyl or chlorine;
$R^2$ is $C_1$–$C_4$-alkylsulfonyl;
$R^3$ is hydrogen, methyl or chlorine;
$R^4$ is hydrogen, methyl, ethyl, chloromethyl or bromomethyl;
$R^5$ is hydrogen or methyl;
in particular is hydrogen; or
$R^4$,$R^5$ together form a methanediyl group;
$R^6$ is hydroxyl;
$R^7$ is $C_1$–$C_4$-alkyl or cyclopropyl;
$R^8$ is hydrogen or $C_1$–$C_4$-alkyl.

Extraordinary preference is given to the compounds of the formula Ia1 (=I where $R^3$, $R^8$=H; $R^6$=OH; $R^7$=$CH_3$), in particular to the compounds Ia1.1 to Ia1.77 of Table 1, where the definitions of the radicals $R^1$ to $R^8$ are of particular importance for the compounds according to the invention not only in combination with one another but also in each case on their own.

TABLE 1

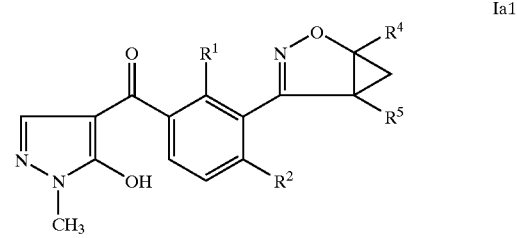

Ia1

| No. | $R^1$ | $R^2$ | $R^4$ | $R^5$ |
|---|---|---|---|---|
| Ia1.1 | Cl | $SO_2CH_3$ | H | H |
| Ia1.2 | Cl | $SO_2CH_3$ | $CH_3$ | H |
| Ia1.3 | Cl | $SO_2CH_3$ | $CH_3$ | $CH_3$ |
| Ia1.4 | Cl | $SO_2CH_3$ | $CH_2CH_3$ | H |

TABLE 1-continued

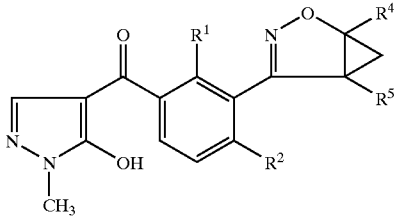

| No. | R¹ | R² | R⁴ | R⁵ |
|---|---|---|---|---|
| Ia1.5 | Cl | SO₂CH₃ | CH₂Cl | H |
| Ia1.6 | Cl | SO₂CH₃ | CH₂F | H |
| Ia1.7 | Cl | SO₂CH₃ | CH₂Br | H |
| Ia1.8 | Cl | SO₂CH₃ | CF₃ | H |
| Ia1.9 | Cl | SO₂CH₃ | CHClCH₃ | H |
| Ia1.10 | Cl | SO₂CH₃ | CHFCH₃ | H |
| Ia1.11 | Cl | SO₂CH₃ | CH₂ | |
| Ia1.12 | CH₃ | SO₂CH₃ | H | H |
| Ia1.13 | CH₃ | SO₂CH₃ | CH₃ | H |
| Ia1.14 | CH₃ | SO₂CH₃ | CH₃ | CH₃ |
| Ia1.15 | CH₃ | SO₂CH₃ | CH₂CH₃ | H |
| Ia1.16 | CH₃ | SO₂CH₃ | CH₂Cl | H |
| Ia1.17 | CH₃ | SO₂CH₃ | CH₂F | H |
| Ia1.18 | CH₃ | SO₂CH₃ | CH₂Br | H |
| Ia1.19 | CH₃ | SO₂CH₃ | CF₃ | H |
| Ia1.20 | CH₃ | SO₂CH₃ | CHClCH₃ | H |
| Ia1.21 | CH₃ | SO₂CH₃ | CHFCH₃ | H |
| Ia1.22 | CH₃ | SO₂CH₃ | CH₂ | |
| Ia1.23 | Cl | CF₃ | H | H |
| Ia1.24 | Cl | CF₃ | CH₃ | H |
| Ia1.25 | Cl | CF₃ | CH₃ | CH₃ |
| Ia1.26 | Cl | CF₃ | CH₂CH₃ | H |
| Ia1.27 | Cl | CF₃ | CH₂Cl | H |
| Ia1.28 | Cl | CF₃ | CH₂F | H |
| Ia1.29 | Cl | CF₃ | CH₂Br | H |
| Ia1.30 | Cl | CF₃ | CF₃ | H |
| Ia1.31 | Cl | CF₃ | CHClCH₃ | H |
| Ia1.32 | Cl | CF₃ | CHFCH₃ | H |
| Ia1.33 | Cl | CF₃ | CH₂ | |
| Ia1.34 | CH₃ | CF₃ | H | H |
| Ia1.35 | CH₃ | CF₃ | CH₃ | H |
| Ia1.36 | CH₃ | CF₃ | CH₃ | CH₃ |
| Ia1.37 | CH₃ | CF₃ | CH₂CH₃ | H |
| Ia1.38 | CH₃ | CF₃ | CH₂Cl | H |
| Ia1.39 | CH₃ | CF₃ | CH₂F | H |
| Ia1.40 | CH₃ | CF₃ | CH₂Br | H |
| Ia1.41 | CH₃ | CF₃ | CF₃ | H |
| Ia1.42 | CH₃ | CF₃ | CHClCH₃ | H |
| Ia1.43 | CH₃ | CF₃ | CHFCH₃ | H |
| Ia1.44 | CH₃ | CF₃ | CH₂ | |
| Ia1.45 | CH₂CH₃ | SO₂CH₃ | H | H |
| Ia1.46 | CH₂CH₃ | SO₂CH₃ | CH₃ | H |
| Ia1.47 | CH₂CH₃ | SO₂CH₃ | CH₃ | CH₃ |
| Ia1.48 | CH₂CH₃ | SO₂CH₃ | CH₂CH₃ | H |
| Ia1.49 | CH₂CH₃ | SO₂CH₃ | CH₂Cl | H |
| Ia1.50 | CH₂CH₃ | SO₂CH₃ | CH₂F | H |
| Ia1.51 | CH₂CH₃ | SO₂CH₃ | CH₂Br | H |
| Ia1.52 | CH₂CH₃ | SO₂CH₃ | CF₃ | H |
| Ia1.53 | CH₂CH₃ | SO₂CH₃ | CHClCH₃ | H |
| Ia1.54 | CH₂CH₃ | SO₂CH₃ | CHFCH₃ | H |
| Ia1.55 | CH₂CH₃ | SO₂CH₃ | CH₂ | |
| Ia1.56 | CH₃ | SO₂CH₂CH₃ | H | H |
| Ia1.57 | CH₃ | SO₂CH₂CH₃ | CH₃ | H |
| Ia1.58 | CH₃ | SO₂CH₂CH₃ | CH₃ | CH₃ |
| Ia1.59 | CH₃ | SO₂CH₂CH₃ | CH₂CH₃ | H |
| Ia1.60 | CH₃ | SO₂CH₂CH₃ | CH₂Cl | H |
| Ia1.61 | CH₃ | SO₂CH₂CH₃ | CH₂F | H |
| Ia1.62 | CH₃ | SO₂CH₂CH₃ | CH₂Br | H |
| Ia1.63 | CH₃ | SO₂CH₂CH₃ | CF₃ | H |
| Ia1.64 | CH₃ | SO₂CH₂CH₃ | CHClCH₃ | H |
| Ia1.65 | CH₃ | SO₂CH₂CH₃ | CHFCH₃ | H |
| Ia1.66 | CH₃ | SO₂CH₂CH₃ | CH₂ | |
| Ia1.67 | Cl | SO₂CH₂CH₃ | H | H |
| Ia1.68 | Cl | SO₂CH₂CH₃ | CH₃ | H |

TABLE 1-continued

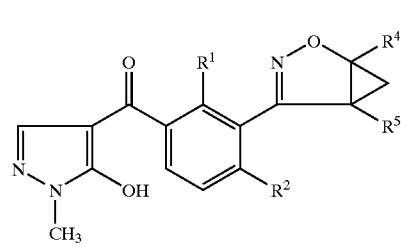

| No. | R¹ | R² | R⁴ | R⁵ |
|---|---|---|---|---|
| Ia1.69 | Cl | SO₂CH₂CH₃ | CH₃ | CH₃ |
| Ia1.70 | Cl | SO₂CH₂CH₃ | CH₂CH₃ | H |
| Ia1.71 | Cl | SO₂CH₂CH₃ | CH₂Cl | H |
| Ia1.72 | Cl | SO₂CH₂CH₃ | CH₂F | H |
| Ia1.73 | Cl | SO₂CH₂CH₃ | CH₂Br | H |
| Ia1.74 | Cl | SO₂CH₂CH₃ | CF₃ | H |
| Ia1.75 | Cl | SO₂CH₂CH₃ | CHClCH₃ | H |
| Ia1.76 | Cl | SO₂CH₂CH₃ | CHFCH₃ | H |
| Ia1.77 | Cl | SO₂CH₂CH₃ | CH₂ | |

Extraordinary preference is also given to the compounds of the formula Ia2, in particular to the compounds Ia2.1 to Ia2.77, which differ from the corresponding compounds Ia1.1 to Ia1.77 in that $R^7$ is ethyl.

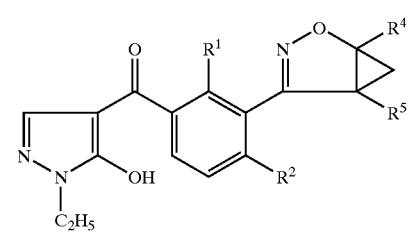

Extraordinary preference is also given to the compounds of the formula Ia3, in particular to the compounds Ia3.1 to Ia3.77, which differ from the corresponding compounds Ia1.1 to Ia1.77 in that $R^7$ is isopropyl.

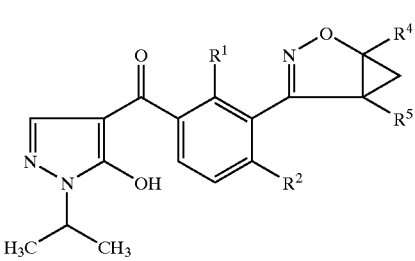

Extraordinary preference is also given to the compounds of the formula Ia4, in particular to the compounds Ia4.1 to Ia4.77, which differ from the corresponding compounds Ia1.1 to Ia1.77 in that $R^7$ is t-butyl.

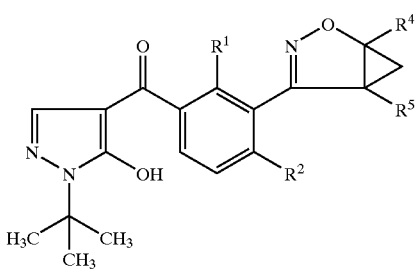

Ia4

Extraordinary preference is also given to the compounds of the formula Ia5, in particular to the compounds Ia5.1 to Ia5.77, which differ from the corresponding compounds Ia1.1 to Ia1.77 in that $R^7$ is cyclopropyl.

Ia5

Extraordinary preference is also given to the compounds of the formula Ia6, in particular to the compounds Ia6.1 to Ia6.77, which differ from the corresponding compounds Ia1.1 to Ia1.77 in that $R^8$ is methyl.

Ia6

Extraordinary preference is also given to the compounds of the formula Ia7, in particular to the compounds Ia7.1 to Ia7.77, which differ from the corresponding compounds Ia1.1 to Ia1.77 in that $R^8$ is methyl and $R^7$ is ethyl.

Ia7

Extraordinary preference is also given to the compounds of the formula Ia8, in particular to the compounds Ia8.1 to Ia8.77, which differ from the corresponding compounds Ia1.1 to Ia1.77 in that $R^8$ is methyl and $R^7$ is isopropyl.

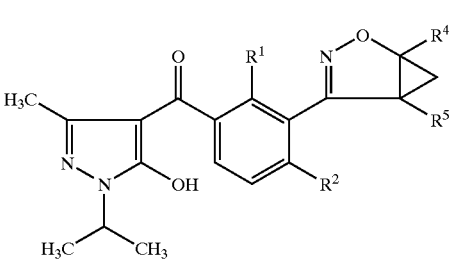

Ia8

Extraordinary preference is also given to the compounds of the formula Ia9, in particular to the compounds Ia9.1 to Ia9.77, which differ from the corresponding compounds Ia1.1 to Ia1.77 in that $R^8$ is methyl and $R^7$ is t-butyl.

Ia9

Extraordinary preference is also given to the compounds of the formula Ia10, in particular to the compounds Ia10.1 to Ia10.77, which differ from the corresponding compounds Ia1.1 to Ia1.77 in that $R^8$ is methyl and $R^7$ is cyclopropyl.

Ia10

Extraordinary preference is also given to the compounds of the formula Ia11, in particular to the compounds Ia11.1 to Ia11.77, which differ from the corresponding compounds Ia1.1 to Ia1.77 in that $R^6$ is phenylcarbonyloxy.

Ia11

Extraordinary preference is also given to the compounds of the formula Ia12, in particular to the compounds Ia12.1 to Ia12.77, which differ from the corresponding compounds Ia1.1 to Ia1.77 in that $R^6$ is phenylcarbonyloxy and $R^7$ is ethyl.

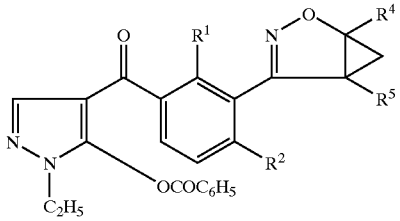

Ia12

Extraordinary preference is also given to the compounds of the formula Ia13, in particular to the compounds Ia13.1 to Ia13.77, which differ from the corresponding compounds Ia1.1 to Ia1.77 in that $R^6$ is phenylcarbonyloxy and $R^7$ is isopropyl.

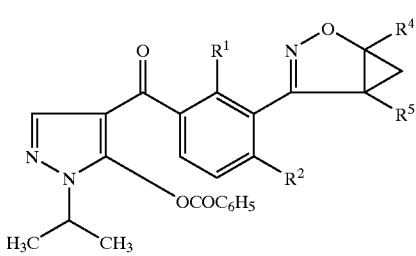

Ia13

Extraordinary preference is also given to the compounds of the formula Ia14, in particular to the compounds Ia14.1 to Ia14.77, which differ from the corresponding compounds Ia1.1 to Ia1.77 in that $R^6$ is phenylcarbonyloxy and $R^7$ is t-butyl.

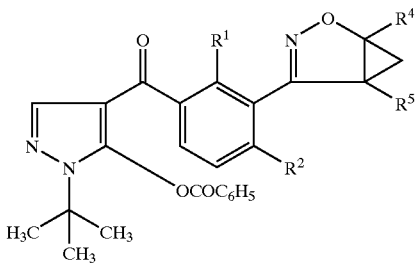

Ia14

Extraordinary preference is also given to the compounds of the formula Ia15, in particular to the compounds Ia15.1 to Ia15.77, which differ from the corresponding compounds Ia1.1 to Ia1.77 in that $R^6$ is 3-fluorophenylcarbonyloxy.

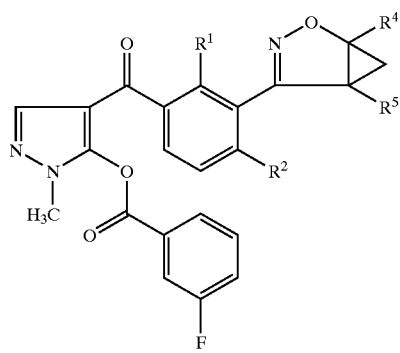

Ia15

Extraordinary preference is also given to the compounds of the formula Ia16, in particular to the compounds Ia16.1 to Ia16.77, which differ from the corresponding compounds Ia1.1 to Ia1.77 in that $R^6$ is 3-fluorophenylcarbonyloxy and $R^7$ is ethyl.

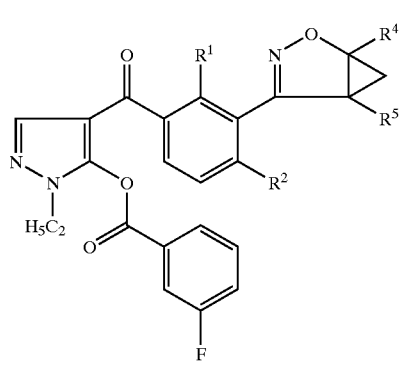

Ia16

Extraordinary preference is also given to the compounds of the formula Ia17, in particular to the compounds Ia17.1 to Ia17.77, which differ from the corresponding compounds Ia1.1 to Ia1.77 in that $R^6$ is 3-fluorophenylcarbonyloxy and $R^7$ is isopropyl.

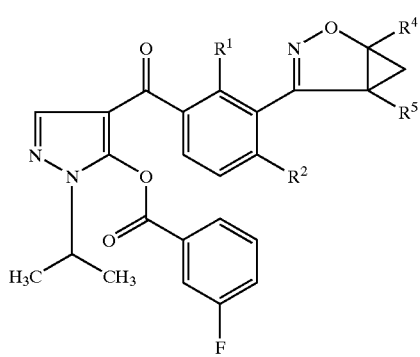

Ia17

Extraordinary preference is also given to the compounds of the formula Ia18, in particular to the compounds Ia18.1 to Ia18.77, which differ from the corresponding compounds Ia1.1 to Ia1.77 in that $R^6$ is 3-fluorophenylcarbonyloxy and $R^7$ is t-butyl.

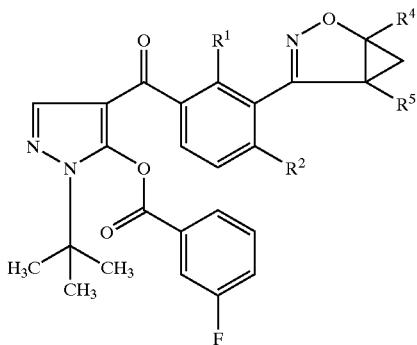

Ia18

Extraordinary preference is also given to the compounds of the formula Ia19, in particular to the compounds Ia19.1 to Ia19.77, which differ from the corresponding compounds Ia1.1 to Ia1.77 in that $R^6$ is 3-trifluoromethylphenylcarbonyloxy.

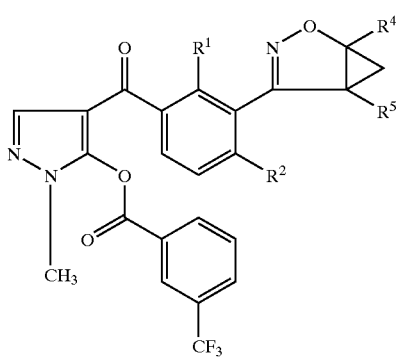

Ia19

Extraordinary preference is also given to the compounds of the formula Ia20, in particular to the compounds Ia20.1 to Ia20.77, which differ from the corresponding compounds Ia1.1 to Ia1.77 in that $R^6$ is 3-trifluoromethylphenylcarbonyloxy and $R^7$ is ethyl.

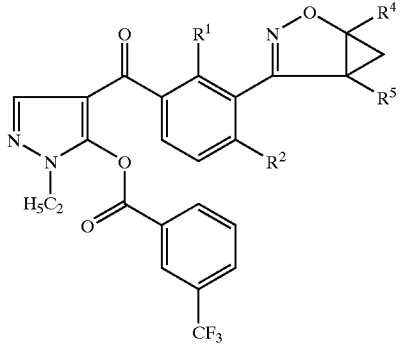

Ia20

Extraordinary preference is also given to the compounds of the formula Ia21, in particular to the compounds Ia21.1 to Ia21.77, which differ from the corresponding compounds Ia1.1 to Ia1.77 in that $R^6$ is 3-trifluoromethylphenylcarbonyloxy and $R^7$ is isopropyl.

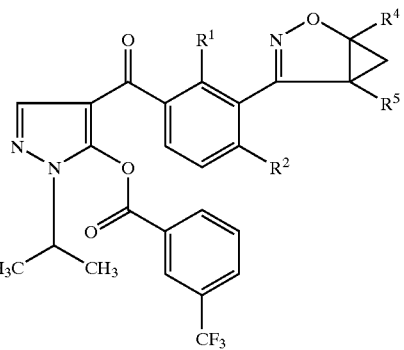

Ia21

Extraordinary preference is also given to the compounds of the formula Ia22, in particular to the compounds Ia22.1 to Ia22.77, which differ from the corresponding compounds Ia1.1 to Ia1.77 in that $R^6$ is 3-trifluoromethylphenylcarbonyloxy and $R^7$ is t-butyl.

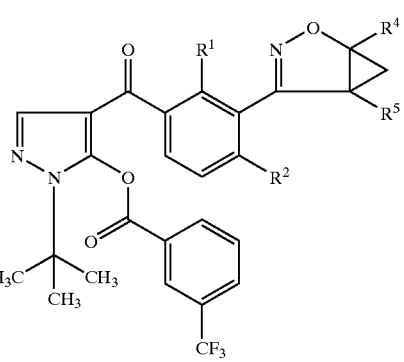

Ia22

Extraordinary preference is also given to the compounds of the formula Ia23, in particular to the compounds Ia23.1 to Ia23.77, which differ from the corresponding compounds Ia1.1 to Ia1.77 in that $R^6$ is 3-chlorophenylcarbonyloxy.

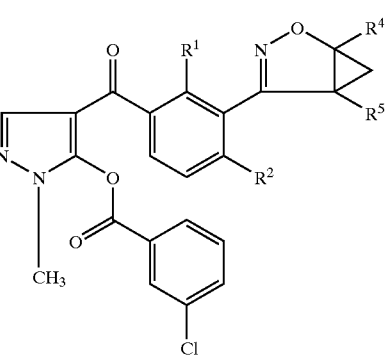

Ia23

Extraordinary preference is also given to the compounds of the formula Ia24, in particular to the compounds Ia24.1 to Ia24.77, which differ from the corresponding compounds Ia1.1 to Ia1.77 in that $R^6$ is 3-chlorophenylcarbonyloxy and $R^7$ is ethyl.

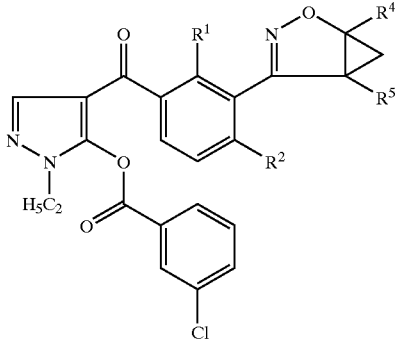

Ia24

Extraordinary preference is also given to the compounds of the formula Ia25, in particular to the compounds Ia25.1 to Ia25.77, which differ from the corresponding compounds Ia1.1 to Ia1.77 in that R⁶ is 3-chlorophenylcarbonyloxy and R⁷ is isopropyl.

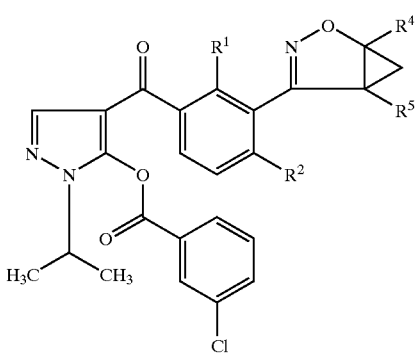

Ia25

Extraordinary preference is also given to the compounds of the formula Ia26, in particular to the compounds Ia26.1 to Ia26.77, which differ from the corresponding compounds Ia1.1 to Ia1.77 in that R⁶ is 3-chlorophenylcarbonyloxy and R⁷ is t-butyl.

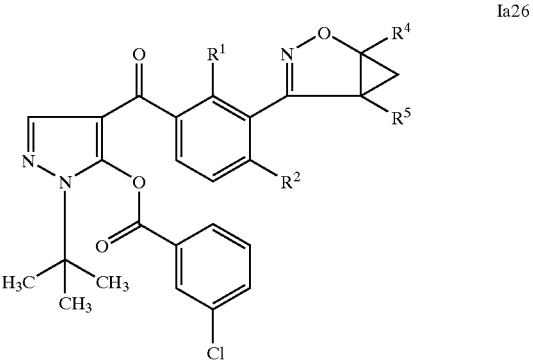

Ia26

The cyclopropyl-fused 3-(4,5-dihydroisoxazol-3-yl)-substituted benzoylpyrazoles of the formula I can be obtained by different routes, for example by the processes below.

Process A:

Compounds of the formula I where $R^6$=OH are obtained by reacting pyrazoles of the formula II with an activated benzoic acid derivative IIIα or a benzoic acid IIIβ, which is preferably activated in situ, to give the corresponding acylation product I' and subsequent rearrangement.

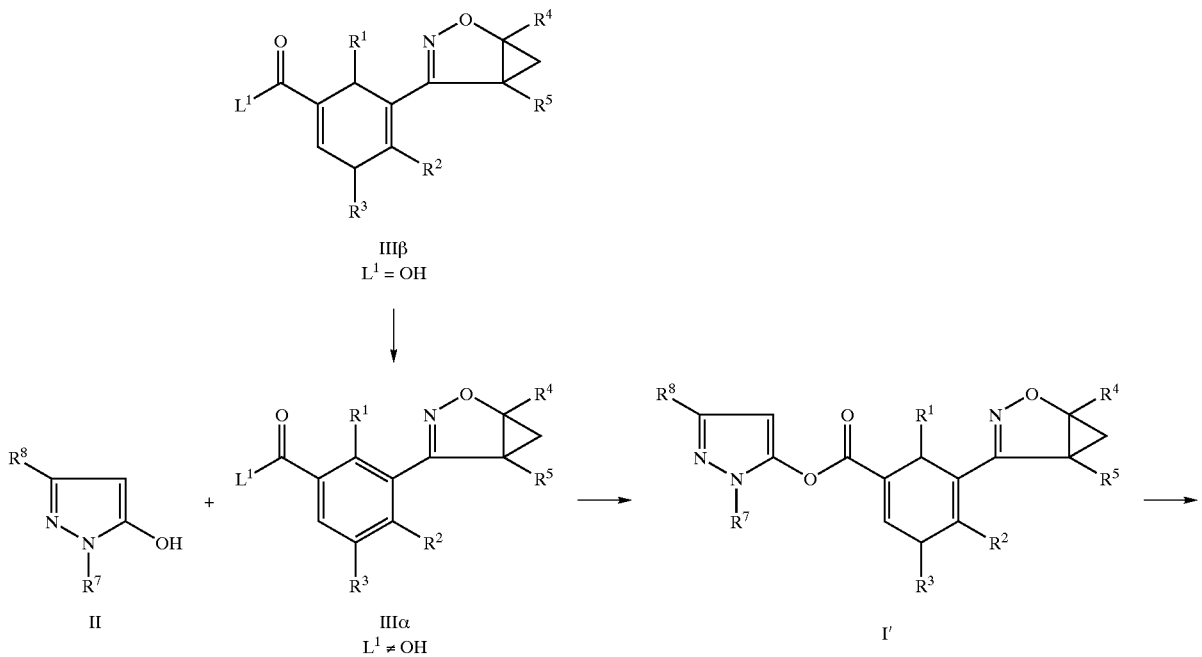

-continued

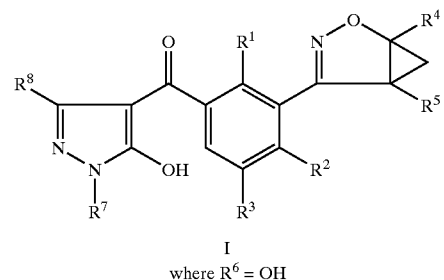

I
where $R^6$ = OH $L^1$ is hydroxyl or a nucleophilically displaceable leaving group, such as halogen, for example bromine or chlorine, hetaryl, for example imidazolyl or pyridyl, carboxylate, for example acetate, trifluoroacetate, etc.

The activated benzoic acid derivative can be employed directly, such as in the case of the benzoyl halides, or be generated in situ, for example using dicyclohexylcarbodiimide, triphenylphosphine/azodicarboxylic ester, 2-pyridine disulfide/triphenylphosphine, carbonyldiimidazole, etc.

It may be advantageous to carry out the acylation reaction in the presence of a base. The reactants and the auxiliary base are in this case advantageously employed in equimolar amounts. A slight excess of auxiliary base, for example from 1.2 to 1.5 molar equivalents, based on II, may be advantageous in certain cases.

Suitable auxiliary bases are tertiary alkylamines, pyridine or alkali metal carbonates. Suitable for use as solvents are, for example, chlorinated hydrocarbons, such as methylene chloride, 1,2-dichloroethane, aromatic hydrocarbons, such as toluene, xylene, chlorobenzene, ethers, such as diethyl ether, methyl tert-butyl ether, dimethoxyethane, tetrahydrofuran, dioxane, polar aprotic solvents, such as acetonitrile, dimethylformamide, dimethyl sulfoxide, or esters, such as ethyl acetate, or mixtures of these.

If the activated carboxylic acid component used is a benzoyl halide, it may be advantageous to cool the reaction mixture to 0–10° C. when adding this reaction partner. The mixture is subsequently stirred at 20–100° C., preferably at 25–50° C., until the reaction has ended. Work-up is carried out in a customary manner, for example by pouring the reaction mixture into water and extracting the product of value. Solvents which are particularly suitable for this purpose are methylene chloride, diethyl ether, dimethoxyethane and ethyl acetate. The organic phase is dried and the solvent is removed, after which the crude ester I' can be employed for the rearrangement without any further purification.

The rearrangement of the esters I' to give the compounds of the formula I is advantageously carried out at 20–40° C. in a solvent and in the presence of a base and, if appropriate, using a cyano compound as catalyst.

Suitable solvents are, for example, acetonitrile, methylene chloride, 1,2-dichloroethane, dioxane, ethyl acetate, dimethoxyethane, tetrahydrofuran, toluene, or mixtures of these. Preferred solvents are acetonitrile and dioxane.

Suitable bases are tertiary amines, such as triethylamine, pyridine, or alkali metal carbonates, such as sodium carbonate or potassium carbonate, which are preferably employed in an equimolar amount or an up to four-fold excess, based on the ester. Preference is given to using triethylamine or alkali metal carbonates, preferably in twice the equimolar amount, based on the ester.

Suitable cyano compounds are inorganic cyanides, such as sodium cyanide and potassium cyanide, and organic cyano compounds, such as acetone cyanohydrin and trimethylsilyl cyanide. They are employed in an amount of from 1 to 50 mol percent, based on the ester. Preference is given to using acetone cyanohydrin or trimethylsilyl cyanide, for example in an amount of from 5 to 15, preferably 10, mol percent, based on the ester.

Work-up can be carried out in a manner known per se. The reaction mixture is, for example, acidified with dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified and the resulting precipitate is filtered off with suction and/or extracted with methylene chloride or ethyl acetate, and the mixture is dried and concentrated. (Examples of the preparation of esters of hydroxypyrazoles and of the rearrangement of the esters are given, for example, in EP-A 282 944 and U.S. Pat. No. 4,643,757).

However, it is also possible to generate the ester I' in situ by reacting a pyrazole of the formula II or an alkali metal salt thereof with a cyclopropyl-fused 3-(4,5-dihydroisoxazol-3-yl)benzene derivative of the formula IV in the presence of carbon monoxide, a catalyst and a base.

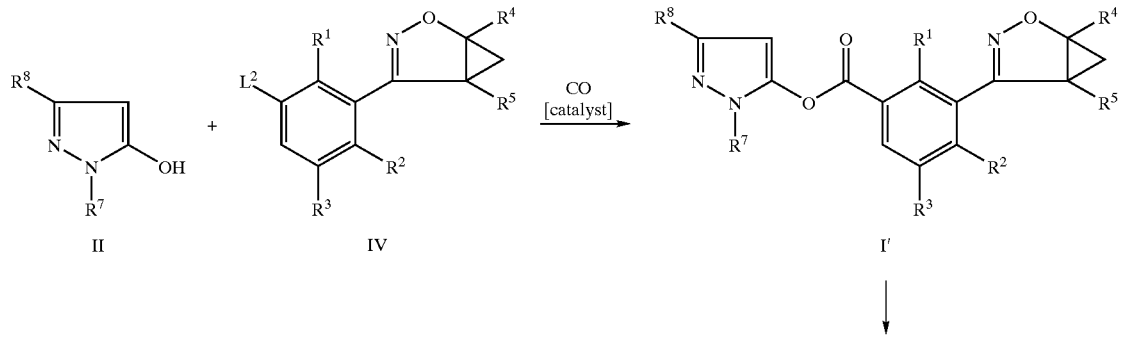

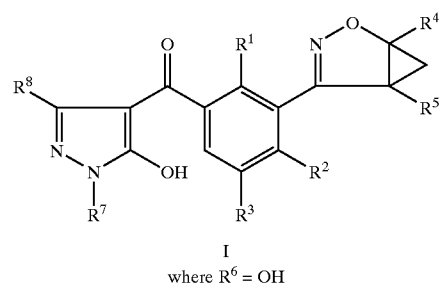

I where $R^6 = OH$ $L^2$ is a leaving group, such as halogen, for example chlorine, bromine or iodine, or sulfonate, such as mesylate or triflate; preference is given to bromine or triflate.

If appropriate, the ester I' is converted directly into the cyclopropyl-fused 3-(4,5-dihydroisoxazol-3-yl)-substituted benzoylpyrazole of the formula I.

Suitable catalysts are palladium-ligand complexes in which the palladium is present in the oxidation stage 0, metallic palladium, which has optionally been absorbed on a support, and preferably palladium(II) salts. The reaction with palladium(II) salts and metallic palladium is preferably carried out in the presence of complex ligands.

An example of a suitable palladium(0) ligand complex is tetrakis(triphenylphosphine)palladium.

Metallic palladium is preferably absorbed on an inert support such as, for example, activated carbon, silica, alumina, barium sulfate or calcium carbonate. The reaction is preferably carried out in the presence of complex ligands such as, for example, triphenylphosphine.

Examples of suitable palladium(II) salts are palladium acetate and palladium chloride. The presence of complex ligands such as, for example, triphenylphosphine is preferred.

Suitable complex ligands for the palladium-ligand complexes, or in whose presence the reaction with metallic palladium or palladium(II) salts is preferably carried out, are tertiary phosphines whose structure is represented by the following formulae:

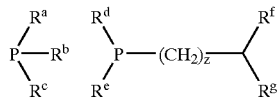

where z is 1 to 4 and the radicals $R^a$ to $R^g$ are $C_1$–$C_6$-alkyl, $C_3$–$C_6$-cycloalkyl, aryl-$C_1$–$C_2$-alkyl or, preferably, aryl. Aryl is, for example, naphthyl and unsubstituted or substituted phenyl such as, for example, 2-tolyl and, in particular, unsubstituted phenyl.

The complex palladium salts can be prepared in a manner known per se starting from commercially available palladium salts such as palladium chloride or palladium acetate and the appropriate phosphines, such as, for example, triphenylphosphine, tricyclohexylphosphine or 1,2-bis(diphenylphosphino)ethane. Many of the complexed palladium salts are also commercially available. Preferred palladium salts are [(R)(+)2,2'-bis(diphenylphosphino)-1,1'-binaphthyl]palladium(II) chloride, bis(triphenylphosphine) palladium(II) acetate and, in particular, bis(triphenylphosphine)palladium(II) chloride.

The palladium catalyst is usually employed in a concentration of from 0.05 to 5 mol %, and preferably 1–3 mol %.

Suitable bases are tertiary amines, such as, for example, N-methylpiperidine, ethyldiisopropylamine, 1,8-bisdimethylaminonaphthalene or, in particular, triethylamine. Also suitable is alkali metal carbonate, such as sodium carbonate or potassium carbonate. However, mixtures of potassium carbonate and triethylamine are also suitable.

In general, from 2 to 4 molar equivalents, in particular 2 molar equivalents, of the alkali metal carbonate, and from 1 to 4 molar equivalents, in particular 2 molar equivalents, of the tertiary amine are employed, based on the cyclopropyl-fused 3-(4,5-dihydroisoxazol-3-yl)benzene derivative of the formula IV.

Suitable solvents are nitriles, such as benzonitrile and acetonitrile, aromatic hydrocarbons, such as toluene, amides, such as dimethylformamide, dimethylacetamide, tetra-$C_1$–$C_4$-alkylureas or N-methylpyrrolidone and, preferably, ethers, such as tetrahydrofuran and methyl tert-butyl ether. Particular preference is given to ethers, such as 1,4-dioxane and dimethoxyethane, as solvents.

The compounds of the formula IIIb can be obtained, for example, as follows:

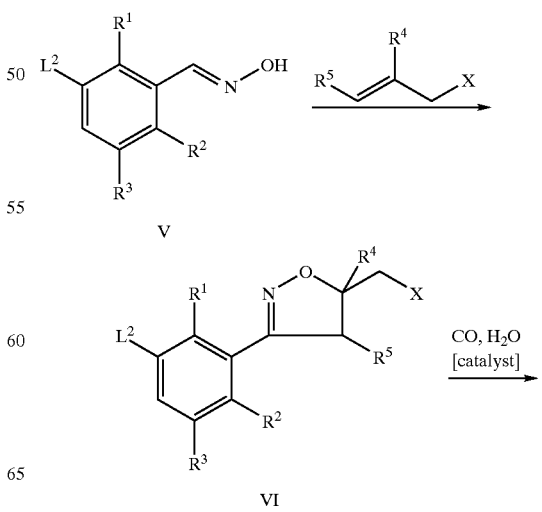

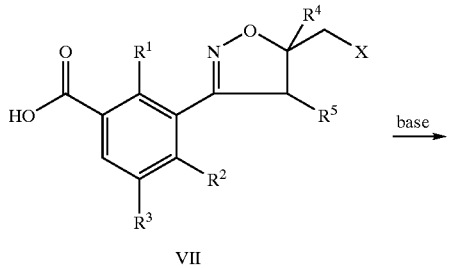

VII

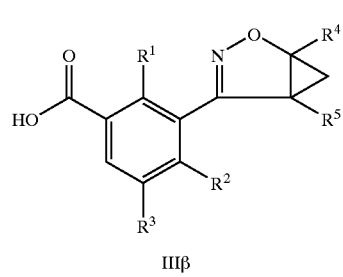

IIIβ

The oximes of the formula V can be converted into the 4,5-dihydroisoxazol-3-yl-benzene derivatives VI in a manner known per se via the hydroxamic acid halide, in particular hydroxamic acid chloride, intermediates. From these, nitrile oxides are prepared in situ, and these nitrile oxides react with alkenes to give the desired products (cf., for example, Chem. Ber. 106 (1973), 3258–3274). Thus, for example, the oxime V is oxidized using sodium hypochlorite and reacted with an allyl halide, for example allyl chloride, in an inert solvent, such as methylene chloride, chloroform, tetrahydrofuran, dioxane or acetonitrile, to give the (4,5-dihydroisoxazol-3-yl)benzene derivative VI. This is then reacted in the presence of a catalyst and a base with carbon monoxide and water to give VII.

$L^2$ is a leaving group, such as halogen, for example chlorine, bromine or iodine, or sulfonate, such as mesylate or triflate; preference is given to bromine or triflate.

X is halogen, preferably chlorine or bromine.

Suitable catalyst systems are the palladium-ligand complexes described above. The reaction conditions are similar.

Ring closure of the cyclopropane ring, i.e. conversion of the compound VII into the compound IIIβ, is carried out using strong bases, such as alkali metal alkoxides, for example potassium tert-butoxide, preferably in polar aprotic solvents, such as dimethyl sulfoxide.

Ring closure of the cyclopropane ring can also be carried out at the stage of the compound VI giving the compound IV, which can be reacted further in a similar manner using carbon monoxide and water in the presence of a catalyst and base to give IIIβ.

It is also possible to obtain the compounds of the formula IIIβ by converting an oxime of the formula VIII into the corresponding hydroxamic acid halide, in particular hydroxamic acid chloride, generating a nitrile oxide in situ and reacting this with an alkene (cf., for example, Chem. Ber. 106 (1973), 3258–3274). The ester is then hydrolyzed under conditions known per se to give the (4,5-dihydroisoxazol-3-yl)benzene VII and reacted further as described above.

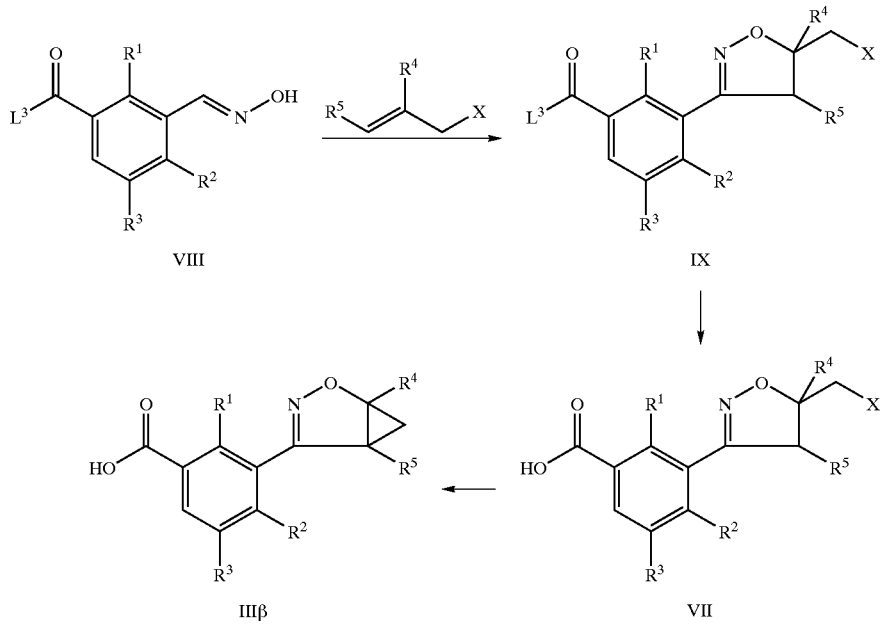

$L^3$ is a $C_1$–$C_6$-alkoxy radical and X is halogen, preferably chlorine or bromine.

Compounds of the formula I where $R^6$≠hydroxyl are obtained by reacting compounds of the formula I where $R^6$=hydroxyl with alkylating agents, sulfonylating agents or acylating agents $L^4$—$R^{6a}$(X).

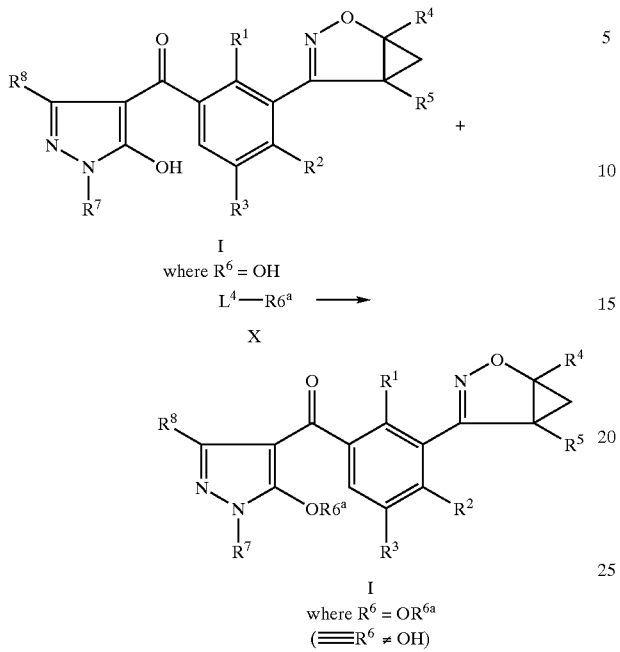

where $R^6$ = OH $L^4$—$R^{6a}$ ⟶

X where $R^6$ = $OR^{6a}$ (≡$R^6$ ≠ OH)

$L^4$ is a nucleophilically displaceable leaving group, such as halogen, for example bromine or chlorine, acyloxy, for example acetyloxy or ethylcarbonyloxy, or alkylsulfonyloxy, for example methylsulfonyloxy or trifluoromethylsulfonyloxy.

$R^{6a}$ is $C_1$–$C_6$-alkyl, $C_3$–$C_6$-alkenyl, $C_1$–$C_6$-alkylsulfonyl, $C_1$–$C_6$-alkylcarbonyl, phenyl-$C_1$–$C_4$-alkyl, phenylcarbonyl-$C_1$–$C_4$-alkyl, phenylsulfonyl or phenylcarbonyl, where the phenyl radical of the four lastmentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy.

The compounds of the formula X can be employed directly, such as, for example, in the case of the sulfonyl halides or sulfonic anhydrides, or be generated in situ, for example activated sulfonic acids (using sulfonic acid and dicyclohexylcarbodiimide, carbonyldiimidazole, etc.).

The starting materials are generally employed in an equimolar ratio. However, it may also be advantageous to employ an excess of one or the other component.

If appropriate, it may be advantageous to carry out the reaction in the presence of a base. The reactants and the auxiliary base are advantageously employed in equimolar amounts. An excess of auxiliary base, for example from 1.5 to 3 molar equivalents, based on I (where $R^6$=OH), may be advantageous in certain cases.

Suitable auxiliary bases are tertiary alkylamines, such as triethylamine, pyridine, alkali metal carbonates, for example sodium carbonate, potassium carbonate, and alkali metal hydrides, for example sodium hydride. Preference is given to using triethylamine and pyridine.

Suitable solvents are, for example, chlorinated hydrocarbons, such as methylene chloride, 1,2-dichloroethane, aromatic hydrocarbons, for example toluene, xylene, chlorobenzene, ethers, such as diethyl ether, methyl tert-butyl ether, tetrahydrofuran, dioxane, polar aprotic solvents, such as acetonitrile, dimethylformamide, dimethyl sulfoxide, or esters, such as ethyl acetate, or mixtures of these.

In general, the reaction temperature is in the range from 0° C. to the boiling point of the reaction mixture.

Work-up can be carried out in a manner known per se to give the product.

The pyrazoles of the formula II are known or can be prepared by processes known per se (for example EP-A 240 001 and J. Prakt. Chem. 315 (1973), 383).

The compounds of the formulae III and IV as such are in each case novel

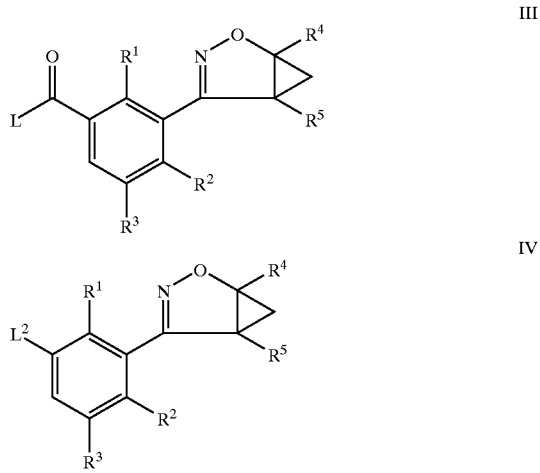

where in each case the variables $R^1$ to $R^5$ are as defined under the compounds of the formula I and L is hydroxyl or a radical which can be removed by hydrolysis; and $L^2$ is a nucleophilically displaceable leaving group.

Examples of radicals which can be removed by hydrolysis are alkoxy, phenoxy, alkylthio and phenylthio radicals which may be substituted or unsubstituted, halides, hetaryl radicals attached via nitrogen, amino and imino radicals which may be substituted or unsubstituted, etc.

Examples of nucleophilically displaceable leaving groups are halogen, $C_1$–$C_4$-alkylsulfonyloxy and $C_1$–$C_4$-haloalkylsulfonyloxy.

Preferred compounds of the formula III are those in which L is halogen, in particular chlorine or bromine.

Preference is also given to those compounds of the formula III in which L is hydroxyl.

Preference is also given to those compounds of the formula III in which L is $C_1$–$C_6$-alkoxy.

With respect to the variables $R^1$ to $R^5$, the particularly preferred embodiments of the compounds of the formulae III and IV correspond to those of the cyclopropyl-fused 3-(4,5-dihydroisoxazol-3-yl)-substituted benzenepyrazoles of the formula I.

Process B:

Alternatively, the compounds of the formula I where $R^6$=OH can be prepared as follows:

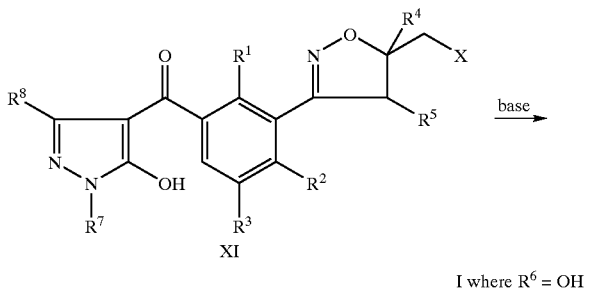

I where $R^6$ = OH

Suitable bases and solvents are those mentioned above for the ring closure.

The compounds of the formula I where $R^6$=OH can be converted as discussed above by reaction with alkylating agents, sulfonylating agents or acylating agents $L^4$—$R^{6a}$(X) into compounds of the formula I where $R^6$=OH.

PREPARATION EXAMPLES

4-[2-Methyl-3-(2-oxa-3-azabicyclo[3.1.0]hex-3-en-4-yl)-4-methyl-sulfonylbenzoyl]-5-hydroxy-1-methyl-1H-pyrazole (compound 2.3)

Step a)

At 15–20° C., 3.04 g of potassium tert-butoxide were added to a solution of 3.0 g (9 mmol) of 2-methyl-3-(5-chloromethyl-4,5-dihydroisoxazol-3-yl)-4-methylsulfonylbenzoic acid in 5 ml of dimethyl sulfoxide, and the mixture was stirred at room temperature overnight. The reaction mixture was stirred into 0.3 l of 3% strength hydrochloric acid and extracted three times with ethyl acetate. The combined organic phases were washed with water and dried, and the solvent was removed. The residue was purified by silica gel column chromatography (mobile phase=toluene/tetrahydrofuran/acetic acid 8/2/1). This gave 1.3 g (49% of theory) of 2-methyl-3-(2-oxa-3-azabicyclo[3.1.0]hex-3-en-4-yl)-4-methylsulfonylbenzoic acid. The $^1$H-NMR spectrum corresponded to the given structure.

Step b)

Under an atmosphere of nitrogen, 0.79 g (3.9 mmol) of dicyclohexylcarbodiimide was added to a solution of 0.75 g (2.54 mmol) of the product from step a) and 0.25 g (2.54 mmol) of 1-methyl-5-hydroxy-1H-pyrazole in 50 ml of anhydrous acetonitrile, and the mixture was stirred at 40° C. for 2 hours and at room temperature for a further 12 hours. The solvent was evaporated under reduced pressure and the residue was taken up in ethyl acetate, extracted three times with 5% strength potassium carbonate solution, washed three times with water, dried and concentrated to dryness. This gave 1.2 g of a viscous brown oil which was reacted further without purification.

Step c)

A mixture of 1.2 g of the product from step b) and 0.52 g of potassium carbonate in 5 ml of dioxane was stirred at room temperature for 4 hours. The mixture was then concentrated to dryness under reduced pressure, the residue was taken up in water and the aqueous phase was washed three times with diethyl ether. The pH of the aqueous phase was then adjusted to 1–2 using 10% strength hydrochloric acid and the aqueous phase was extracted three times with ethyl acetate. The combined organic phases were washed with water, dried and concentrated to dryness under reduced pressure. This gave 0.3 g (33% of theory) of an amorphous foam. The $^1$H-NMR spectrum corresponded to the given structure of the title compound.

4-[2-Methyl-3-(2-oxa-3-aza-bicyclo[3.1.0]hex-3-en-4-yl)-4-methylsulfonylbenzoyl]-5-hydroxy-1-tert-butyl-1H-pyrazole (compound 2.1)

At room temperature, 0.17 g (1.50 mmol) of potassium tert-butoxide was added to a solution of 0.23 g (0.51 mmol) of 4-[2-methyl-3-(5-chloromethyl-4,5-dihydroisoxazol-3-yl)-4-methylsulfonylbenzoyl]-5-hydroxy-1-tert-butyl-1H-pyrazole in 2.5 ml of dimethyl sulfoxide, and the mixture was stirred overnight. The mixture was then stirred into 300 ml of 3% strength aqueous hydrochloric acid, the aqueous phase was extracted three times with in each case 200 ml of ethyl acetate and the combined organic phases were washed four times with in each case 50 ml of water, dried over sodium sulfate and concentrated under reduced pressure. This gave 0.12 g (57%) of the title compound in the form of a brown solid of melting point 69–74° C.

$^1$H-NMR (δ in ppm): δ=1.1–1.3 (m, 2H), 1.58 (s, 9H), 2.58 (s, 3H), 2.3–2.5 (m, 1H), 3.22 (s, 3H), 5.21 (m, 1H), 7.32 (s, 1H), 7.72 (d, 1H), 8.11 (d, 1H).

In addition to the compound above, Table 2 lists further cyclopropyl-fused 3-(4,5-dihydroisoxazol-3-yl)-substituted benzoylpyrazoles of the formula I which were prepared or are preparable in a similar manner.

TABLE 2

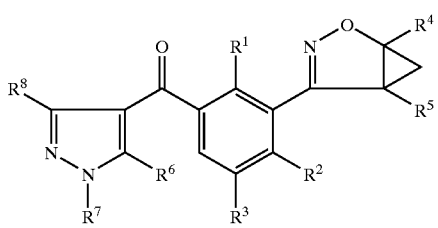

| No. | $R^1$ | $R^2$ | $R^3$ | $R^4$ | $R^5$ | $R^6$ | $R^7$ | $R^8$ | Physical data m.p. [° C.] |
|---|---|---|---|---|---|---|---|---|---|
| 2.1 | $CH_3$ | $SO_2CH_3$ | H | H | H | OH | $C(CH_3)_3$ | H | 69–74 |
| 2.2 | $CH_3$ | $SO_2CH_3$ | H | H | H | OH | $C_2H_5$ | H | 94–97 |

TABLE 2-continued

| No. | $R^1$ | $R^2$ | $R^3$ | $R^4$ | $R^5$ | $R^6$ | $R^7$ | $R^8$ | Physical data m.p. [° C.] |
|---|---|---|---|---|---|---|---|---|---|
| 2.3 | $CH_3$ | $SO_2CH_3$ | H | H | H | OH | $CH_3$ | H | 106–112 |
| 2.4 | $CH_3$ | $SO_2CH_3$ | H | H | H | OH | $CH(CH_3)_2$ | H | 90–95 |
| 2.5 | $CH_3$ | $SO_2CH_3$ | H | H | H | OH | $CH_3$ | $CH_3$ | 89–91 |
| 2.6 | $CH_3$ | $SO_2CH_3$ | H | $CH_2Cl$ | H | OH | $CH_2CH_3$ | H | 99–103 |
| 2.7 | $CH_3$ | $SO_2CH_3$ | H | $CH_3$ | H | OH | $CH_3$ | H | 98–102 |
| 2.8 | $CH_3$ | $SO_2CH_3$ | H | —$CH_2$— | | OH | $CH(CH_3)_2$ | H | 115–119 |
| 2.9 | $CH_3$ | $SO_2CH_3$ | H | —$CH_2$— | | OH | $C(CH_3)_3$ | H | 136–140 |
| 2.10 | $CH_3$ | $SO_2CH_3$ | H | $CH_3$ | H | OH | $C(CH_3)_3$ | H | 90–95 |
| 2.11 | $CH_3$ | $SO_2CH_3$ | H | $CH_3$ | H | OH | $CH(CH_3)_2$ | H | 67–70 |
| 2.12 | $CH_3$ | $SO_2CH_3$ | H | $CH_3$ | H | OH | cyclo-$C_3H_5$ | H | 71–79 |
| 2.13 | $CH_3$ | $SO_2CH_3$ | H | H | $CH_3$ | OH | $CH_3$ | H | 99–103 |
| 2.14 | $CH_3$ | $SO_2CH_3$ | H | H | $CH_3$ | OH | $CH(CH_3)_2$ | H | 75–80 |
| 2.15 | $CH_3$ | $SO_2CH_3$ | H | H | $CH_3$ | OH | cyclo-$C_3H_5$ | H | 65–70 |
| 2.16 | $CH_3$ | $SO_2CH_3$ | H | H | $CH_3$ | OH | $C(CH_3)_3$ | H | 110–115 |

The cyclopropyl-fused 3-(4,5-dihydroisoxazol-3-yl)-substituted benzoylpyrazoles of the formula I and their agriculturally useful salts are suitable, both in the form of isomer mixtures and in the form of the pure isomers, as herbicides. The herbicidal compositions comprising compounds of the formula I control vegetation on non-crop areas very efficiently, especially at high rates of application. They act against broad-leaved weeds and harmful grasses in crops such as wheat, rice, maize, soya and cotton without causing any significant damage to the crop plants. This effect is mainly observed at low rates of application.

Depending on the application method used, the compounds of the formula I, or herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N.rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

In addition, the compounds of the formula I may also be used in crops which tolerate the action of herbicides owing to breeding, including genetic engineering methods.

The compounds of the formula I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting or granules, by means of spraying, atomizing, dusting, broadcasting or watering. The use forms depend on the intended aims; in any case, they should ensure a very fine distribution of the active compounds according to the invention.

The herbicidal compositions comprise a herbicidally effective amount of at least one compound of the formula I or an agriculturally useful salt of I and auxiliaries customarily used for formulating crop protection agents.

Essentially, suitable inert auxiliaries include: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, or strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the cyclopropyl-fused 3-(4,5-dihydroisoxazol-3-yl)-substituted benzoylpyrazoles, either as such or dissolved in an oil or solvent, can be homogenized in water by means of a wetting agent, tackifier, dispersant or emulsifier. Alternatively, it is possible to prepare concentrates consisting of active substance, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or grinding the active substances together with a solid carrier.

Granules, e.g. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

The concentrations of the compounds of the formula I in the ready-to-use preparations can be varied within wide ranges. In general, the formulations comprise from about 0.001 to 98% by weight, preferably from 0.01 to 95% by weight of at least one active compound. The active compounds are employed in a purity of from 90% to 100%, preferably from 95% to 100% (according to the NMR spectrum).

The compounds I according to the invention can be formulated, for example, as follows:

I. 20 parts by weight of the compound No. 2.5 are dissolved in a mixture consisting of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. 2.5 are dissolved in a mixture consisting of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the active compound No. 2.5 are dissolved in a mixture consisting of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of the active compound No. 2.5 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the active compound No. 2.5 are mixed with 97 parts by weight of finely divided kaolin. This gives a dust which comprises 3% by weight of the active compound.

VI. 20 parts by weight of the active compound No. 2.5 are mixed intimately with 2 parts by weight of the calcium salt of dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the active compound No. 2.5 is dissolved in a mixture consisting of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the active compound No. 2.5 is dissolved in a mixture consisting of 80 parts by weight of cyclohexanone and 20 parts by weight of Wettol® EM 31 (nonionic emulsifier based on ethoxylated castor oil). This gives a stable emulsion concentrate.

The compounds of the formula I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active compounds reach the leaves of undesirable plants growing underneath, or the bare soil surface (post-directed, lay-by).

The application rates of the compound of the formula I are from 0.001 to 3.0, preferably from 0.01 to 1.0 kg/ha of active substance (a.s.), depending on the control target, the season, the target plants and the growth stage.

To widen the activity spectrum and to achieve synergistic effects, the cyclopropyl-fused 3-(4,5-dihydroisoxazol-3-yl)-substituted benzoylpyrazoles of the formula I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-(het)aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds of the formula I, alone or else concomitantly in combination with other herbicides, or in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

USE EXAMPLES

The herbicidal activity of the cyclopropyl-fused 3-(4,5-dihydroisoxazol-3-yl)-substituted benzoylpyrazoles of the formula I was demonstrated by the following greenhouse experiments:

The cultivation containers used were plastic pots containing loamy sand with approximately 3.0% of humus as the substrate. The seeds of the test plants were sown separately for each species.

For the pre-emergence treatment, directly after sowing the active compounds, which had been suspended or emulsified in water, were applied by means of finely distributing nozzles. The containers were irrigated gently to promote germination and growth and subsequently covered with transparent plastic hoods until the plants had rooted. This cover caused uniform germination of the test plants, unless this was adversely affected by the active compounds.

For the post-emergence treatment, the test plants were first grown to a height of from 3 to 15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to treatment. The application rate for the post-emergence treatment was 0.25 or 0.125 kg of a.s. (active substance)/ha.

Depending on the species, the plants were kept at 10–25° C. or 20–35° C. The test period extended over from 2 to 4 weeks. During this time, the plants were tended, and their response to the individual treatments was evaluated.

The evaluation was carried out using a scale from 0 to 100. 100 means no emergence of the plants, or complete destruction of at least the aerial parts and 0 means no damage, or normal course of growth.

The plants used in the greenhouse experiments were of the following species:

| Scientific name | Common name |
| --- | --- |
| Amaranthus retroflexus | pig weed |
| Avena fatua | wild oat |
| Chenopodium album | lambsquaters |
| Echinochloa crus galli | barnyardgrass |
| Polygonum persicaria | ladysthumb |
| Setaria faberi | giant foxtail |

At application rates of 0.25 or 0.125 kg/ha, the compound No. 2.5 (Table 2) showed very good post-emergence action against the abovementioned undesirable plants.

We claim:
1. A cyclopropyl-fused 3-(4,5-dihydroisoxazol-3-yl)-substituted benzoylpyrazole of the formula I

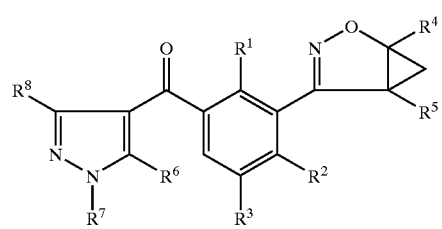

in which
$R^1$ is $C_1-C_6$-alkyl, $C_1-C_6$-haloalkyl, $C_1-C_6$-alkoxy, $C_1-C_6$-haloalkoxy, halogen or nitro;
$R^2$ is $C_1-C_6$-alkyl, $C_1-C_6$-haloalkyl, $C_1-C_6$-alkoxy, $C_1-C_6$-haloalkoxy, $C_1-C_6$-alkylthio, $C_1-C_6$-haloalkylthio, $C_1-C_6$-alkylsulfinyl, $C_1-C_6$-haloalkylsulfinyl, $C_1-C_6$-alkylsulfonyl, $C_1-C_6$-haloalkylsulfonyl, halogen, cyano or nitro;
$R^3$ is hydrogen, $C_1-C_6$-alkyl or halogen;
$R^4$ is hydrogen, $C_1-C_4$-alkyl or $C_1-C_4$-haloalkyl;
$R^5$ may have the meanings given for $R^4$; or
$R^4$, $R^5$ together are a $C_1-C_4$-alkanediyl group which may be partially or fully halogenated and/or may carry one to three $C_1-C_4$-alkyl groups;
$R^6$ is hydroxyl, $C_1-C_6$-alkoxy, $C_3-C_6$-alkenyloxy, $C_1-C_6$-alkylsulfonyloxy, $C_1-C_6$-alkylcarbonyloxy, phenyl-$C_1-C_4$-alkoxy, phenylcarbonyl-$C_1-C_4$-alkoxy, phenylsulfonyloxy, phenylcarbonyloxy, where the phenyl radical of the four lastmentioned substituents may be partially or fully halogenated and/or may carry one to three of the following groups: nitro, cyano, $C_1-C_4$-alkyl, $C_1-C_4$-haloalkyl, $C_1-C_4$-alkoxy or $C_1-C_4$-haloalkoxy;
$R^7$ is hydrogen, $C_1-C_6$-alkyl or cyclopropyl;
$R^8$ is hydrogen, $C_1-C_6$-alkyl or $C_1-C_6$-haloalkyl;
and its agriculturally useful salts.
2. A cyclopropyl-fused 3-(4,5-dihydroisoxazol-3-yl)-substituted benzoylpyrazole as claimed in claim 1 in which $R^1$ is $C_1-C_6$-alkyl or halogen;

$R^2$ is $C_1-C_6$-haloalkyl, $C_1-C_6$-alkylsulfonyl or halogen;

$R^3$ is hydrogen, $C_1-C_4$-alkyl or halogen;

$R^7$ is $C_1-C_4$-alkyl or cyclopropyl;

$R^8$ is hydrogen or $C_1-C_4$-alkyl.

3. A cyclopropyl-fused 3-(4,5-dihydroisoxazol-3-yl)-substituted benzoylpyrazole as claimed in claim 1 in which $R^6$ is hydroxyl, phenyl-$C_1-C_2$-alkoxy, phenylcarbonyl-$C_1-C_2$-alkoxy, phenylsulfonyloxy or phenylcarbonyloxy, where the phenyl radical of the four lastmentioned substituents may be partially or fully halogenated and/or may carry one to three of the following groups: nitro, cyano, $C_1-C_4$-alkyl, $C_1-C_4$-haloalkyl, $C_1-C_4$-alkoxy or $C_1-C_4$-haloalkoxy.

4. A process for preparing cyclopropyl-fused 3-(4,5-dihydroisoxazol-3-yl)-substituted benzoylpyrazoles as claimed in claim 1, which comprises acylating a pyrazole of the formula II

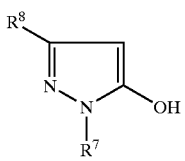

II with a benzoic acid derivative of the formula III,

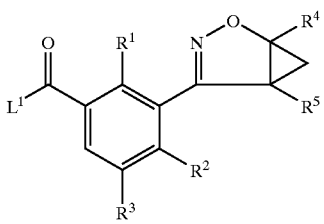

III in which the variables $R^1$ to $R^5$, $R^7$ and $R^8$ are as defined in claim 1 and $L^1$ is hydroxyl or a nucleophilically displaceable leaving group;

rearranging the acylation product to form a compound of the formula I in which $R^6$ is hydroxyl and, if appropriate, reacting the product of the rearrangement with a compound of the formula X $$L^4\text{—}R^{6a} \qquad X$$

in which $L^4$ is a nucleophilically displaceable leaving group; and $R^{6a}$ is $C_1-C_6$-alkyl, $C_3-C_6$-alkenyl, $C_1-C_6$-alkylsulfonyl, $C_1-C_6$-alkylcarbonyl, phenyl-$C_1-C_4$-alkyl, phenylcarbonyl-$C_1-C_4$-alkyl, phenylsulfonyl or phenylcarbonyl, where the phenyl radical of the four lastmentioned substituents may be partially or fully halogenated and/or may carry one to three of the following groups: nitro, cyano, $C_1-C_4$-alkyl, $C_1-C_4$-haloalkyl, $C_1-C_4$-alkoxy or $C_1-C_4$-haloalkoxy.

5. A process for preparing cyclopropyl-fused 3-(4,5-dihydroisoxazol-3-yl)-substituted benzoylpyrazoles as claimed in claim 1, which comprises reacting a pyrazone of the formula II

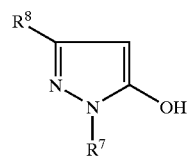

II in which the variables $R^7$ and $R^8$ are as defined in claim 1, or an alkali metal salt thereof, with a cyclopropyl-fused 3-(4,5-dihydroisoxazol-3-yl)-benzene derivative IV

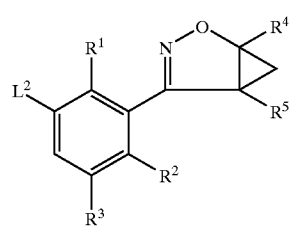

IV where the variables $R^1$ to $R^5$ are as defined in claim 1 and $L^2$ is a leaving group in the presence of carbon monoxide, a catalyst and a base and, if appropriate, reacting the condensation product with a compound of the formula X $$L^4\text{—}R^{6a} \qquad X$$

in which $L^4$ and $R^{6a}$ are as defined in claim 4.

6. A process for preparing cyclopropyl-fused 3-(4,5-dihydroisoxazol-3-yl)-substituted benzoylpyrazoles as claimed in claim 1, which comprises reacting a 3-(5-halomethyl-4,5-dihydroisoxazol-3-yl)-substituted benzoylpyrazole of the formula XI

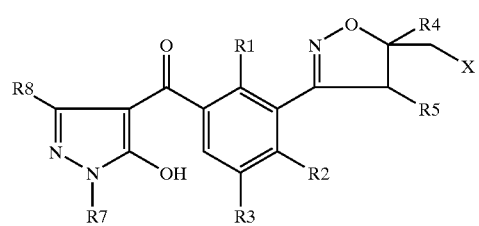

XI in which $R^1$ to $R^5$, $R^7$ and $R^8$ are as defined in claim 1 and X is halogen with a base to give a compound of the formula I in which $R^6$ is hydroxyl and, if appropriate, reacting the reaction product with a compound of the formula X $$L^4\text{—}R^{6a} \qquad X$$

in which $L^4$ and $R^{6a}$ are as defined below $L^4$ is a nucleophilically displaceable leaving group; and $R^{6a}$ is $C_1-C_6$-alkyl, $C_3-C_6$-alkenyl, $C_1-C_6$-alkylsulfonyl, $C_1-C_6$-alkylcarbonyl, phenyl-$C_1-C_4$-alkyl, phenylcarbonyl-$C_1-C_4$-alkyl, phenylsulfonyl or phenylcarbonyl, where the phenyl radical of the four lastmentioned substituents may be partially or fully halogenated and/or may carry one to three of the following groups: nitro cyano, $C_1-C_4$-alkyl, $C_1-C_4$-haloalkyl, $C_1-C_4$-alkoxy or $C_1-C_4$-haloalkoxy.

7. A compound of the formula III or IV

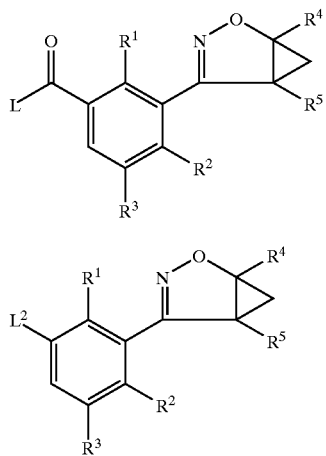

in which $R^1$ to $R^5$ are as defined in claim 1, L is hydroxyl or a radical which can be removed by hydrolysis and $L^2$ is a nucleophilically displaceable leaving group.

8. A composition, comprising a herbicidally effective amount of at least one cyclopropyl-fused 3-(4,5-dihydroisoxazol-3-yl)-substituted benzoylpyrazole of the formula I or an agriculturally useful salt thereof as claimed in claim 1 and auxiliaries customarily used for formulating crop protection agents.

9. A method for controlling undesirable vegetation, which comprises allowing a herbicidally effective amount of at least one cyclopropyl-fused 3-(4,5-dihydroisoxazol-3-yl)-substituted benzoylpyrazole of the formula I or an agriculturally useful salt thereof as claimed in claim 1 to act on plants, their habitat and/or on seeds.

10. A herbicide containing cyclopropyl-fused 3-(4,5-dihydroisoxazol-3-yl)-substituted benzoylpyrazoles of the formula I and/or agriculturally useful salts thereof as claimed in claim 1.

* * * * *